United States Patent
Chen et al.

(10) Patent No.: US 11,447,501 B2
(45) Date of Patent: Sep. 20, 2022

(54) BIPHENYL-CONTAINING DIARYLPYRIMIDO COMPOUNDS, PHARMACEUTICALLY-ACCEPTABLE SALTS THEREOF, COMPOSITION AND PREPARATION THEREOF

(71) Applicant: Fudan University, Shanghai (CN)

(72) Inventors: Fener Chen, Shanghai (CN); Yali Sang, Shanghai (CN); Chunlin Zhuang, Shanghai (CN)

(73) Assignee: Fudan Univeristy, Shanghai (CN)

( * ) Notice: Subject to any disclaimer, the term of this patent is extended or adjusted under 35 U.S.C. 154(b) by 37 days.

(21) Appl. No.: 16/986,200

(22) Filed: Aug. 5, 2020

(65) Prior Publication Data
US 2021/0040109 A1    Feb. 11, 2021

(30) Foreign Application Priority Data

Aug. 6, 2019  (CN) .......................... 201910720006.9

(51) Int. Cl.
| | | |
|---|---|---|
| *C07D 495/04* | (2006.01) | |
| *A61P 31/18* | (2006.01) | |
| *A61K 31/519* | (2006.01) | |

(52) U.S. Cl.
CPC .......... *C07D 495/04* (2013.01); *A61P 31/18* (2018.01); *A61K 31/519* (2013.01)

(58) Field of Classification Search
CPC ..... A61K 31/519; A61P 31/18; C07D 497/04; C07D 487/04
See application file for complete search history.

(56) References Cited

U.S. PATENT DOCUMENTS

2009/0162319 A1*  6/2009  Shaginian ............... A61P 31/12
424/85.5

FOREIGN PATENT DOCUMENTS

| CN | 101343253 A | 1/2009 |
| CN | 109053591 A | 12/2018 |

OTHER PUBLICATIONS

Sang et al. "Follow on-based optimization of the biphenyl-DAPYs as HIV-1 nonnucleoside reverse transcriptase inhibitors against the wide-type and mutant strains," Bioorganic Chemistry, May 2019, vol. 89, 102974. (Year: 2019).*

* cited by examiner

*Primary Examiner* — Shengjun Wang

(57) ABSTRACT

A biphenyl-containing diarylpyrimido compound of formula (I), which is prepared by reacting a 4-chloropyrimidine derivative with a biphenyl derivative in a solvent in the presence of a base. A pharmaceutically-acceptable salt of the compound (I) and a pharmaceutical composition containing the compound (I) or a pharmaceutically-acceptable salt thereof are also provided.

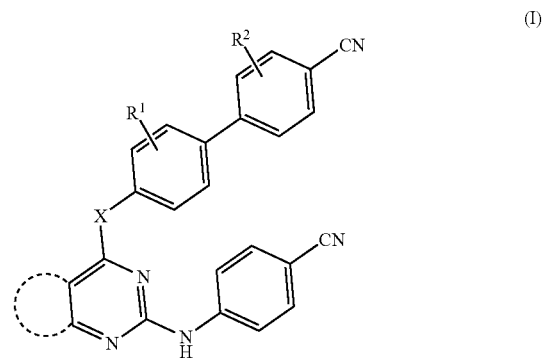

(I)

10 Claims, No Drawings

BIPHENYL-CONTAINING DIARYLPYRIMIDO COMPOUNDS, PHARMACEUTICALLY-ACCEPTABLE SALTS THEREOF, COMPOSITION AND PREPARATION THEREOF

CROSS-REFERENCE TO RELATED APPLICATIONS

This application claims the benefit of priority from Chinese Patent Application No. 201910720006.9, filed on Aug. 6, 2019. The content of the aforementioned application, including any intervening amendments thereto, is incorporated herein by reference in its entirety.

TECHNICAL FIELD

The present application relates to medicines, and more particularly to biphenyl-containing diarylpyrimido compounds and pharmaceutically-acceptable salts thereof, a composition including the same, and a preparation method for the same.

BACKGROUND

Acquired Immunodeficiency Syndrome (AIDS) is caused by human immunodeficiency virus (HIV). Specifically, HIV can destroy human T lymphocytes, and block the cellular and humoral immune responses, exposing the immune system to paralysis. The data published by the Joint United Nations Programme on HIV/AIDS (UNAIDS) in 2019 revealed that there were a total of 37.9 million HIV-infected cases in the world, and in 2018, 1.7 million people became newly infected with HIV, and 770,000 people died of AIDS.

The life cycle of HIV mainly includes: (1) attaching to and fusing gradually with host T lymphocytes, and releasing genomic RNA into host cells; (2) converting HIV RNA into HIV DNA through reverse transcription and integrating the HIV DNA into the host's genome; (3) synthesizing the HIV RNA and HIV protein by transcription and translation with the help of enzymes and substances inside the host cell; and (4) assembling in the host cell and releasing. These released viruses continue to infect new host cells, thereby destroying the host's immune system. There are some enzymes playing a key role in the life cycle, such as fusion enzyme, reverse transcriptase, protease and integrase, where the reverse transcriptase (RT) plays an important role, and thus it is considered as an important target for anti-HIV-1 drugs.

RT inhibitors generally include nucleoside reverse transcriptase inhibitors (NRTIs) and non-nucleoside reverse transcriptase inhibitors (NNRTIs). Nucleoside reverse transcriptase inhibitors compete with the substrate to act on the active site of RT, inhibiting the activity of RT. However, these inhibitors generally have poor selectivity and high toxicity. Non-nucleoside reverse transcriptase inhibitors are a class of noncompetitive inhibitors, which bind to an allosteric binding pocket (also called non-nucleoside reverse transcriptase inhibitors binding pocket (NNIBP)) about 10 Å away from the active site of the reverse transcriptase. Due to the high selectivity and good activity, NNRTIs have been widely applied to the clinical treatment, and currently, the NNRTIs used in clinic are mainly the second-generation HIV inhibitors, such as diarylpyrimidine compounds, rilpivirine (RPV) and etravirine (ETR).

However, the clinical use of RPV and ETR is greatly limited by the poor water solubility (ETR, <<1 g/mL; RPV, 20 ng/mL), low response rate (ETR, 36.5%; RPV, 27.3%), and side effects appearing in the long-term use. In addition, the amino acid residues on the reverse transcriptase may experience a mutation, which will make the originally effective drugs inactive, that is, the HIV strains possess drug resistance. Therefore, extensive researches have been conducted on the development of a new and highly-effective broad-spectrum non-nucleoside reverse transcriptase inhibitor against drug-resistant virus strains.

Given the above, the present disclosure optimizes the structure of RPV and ETR by introducing a biphenyl structure and a pyrimidine ring, which enhances the non-polar interaction between the compounds and the amino acids on the inner wall of NNIBP, improving the biological activity of these compounds against drug-resistant virus strains.

SUMMARY

An object of the present disclosure is to provide biphenyl-containing diarylpyrimido compounds with strong biological activity, low cytotoxicity and high selectivity t, and its preparation and application.

Technical solutions of the disclosure are described as follows.

In a first aspect, the disclosure provides a biphenyl-containing diarylpyrimido compound of formula (I):

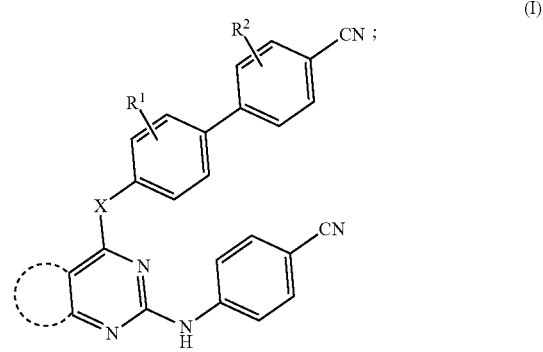

(I)

wherein:

$R^1$ and $R^2$ are independently selected from the group consisting of hydrogen, cyano, nitro, hydroxyl, halogen, amino, $C_3$-$C_6$ cycloalkoxy, $C_3$-$C_6$ cycloalkylamino, substituted $C_1$-$C_6$ alkyl, substituted $C_2$-$C_6$ alkenyl, substituted $C_2$-$C_6$ alkynyl, $C_1$-$C_6$ alkoxy, carboxyl, ester group, amido and sulfonamido;

X is selected from the group consisting of —CH$_2$—, —NH—, —O—, —S—, —S(O)— and —S(O)$_2$—; and ⟨ ⟩ s selected from the group consisting of unsubstituted and substituted benzene ring; thiophene, thiazole, pyrrole, pyrazole, pyran, imidazole, oxazole, isoxazole, pyrazolone, furan, pyridine, azine and an oxide thereof; cyclopentadiene; tetrahydrothiophene; sulphoxide; sulfone; tetrahydrofuran; and substituted cycloalkane.

In a second aspect, the disclosure provides a preparation method of the biphenyl-containing diarylpyrimido compound, comprising:

reacting a 4-chloropyrimidine derivative (II) with a biphenyl derivative (III) in a solvent in the presence of a base to obtain the compound (I), as shown in the following scheme:

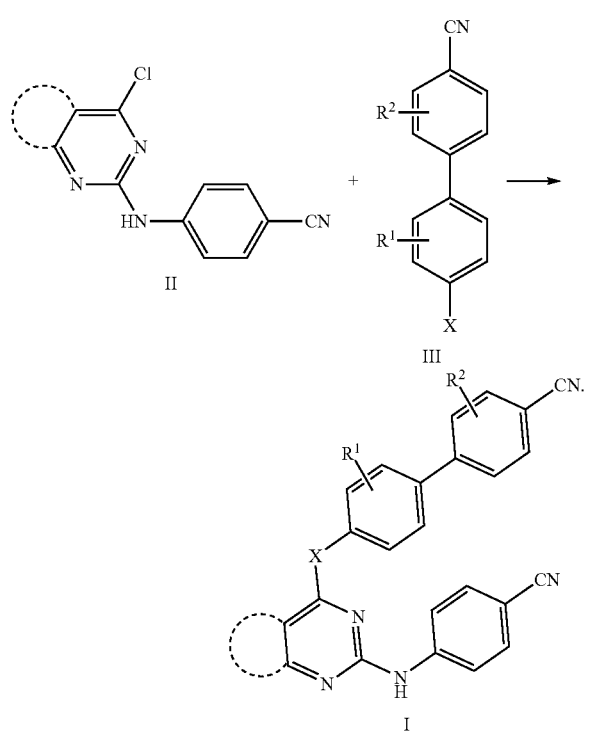

In some embodiments, the solvent is selected from the group consisting of acetone, acetonitrile, toluene, dichloromethane, tetrahydrofuran, N,N-dimethylformamide, N,N-dimethylacetamide, ethanol, isopropanol, n-butanol, isobutanol and a combination thereof.

In some embodiments, the base is an inorganic base or an organic base; wherein the inorganic base is selected from the group consisting of sodium carbonate, potassium carbonate, cesium carbonate, sodium hydroxide, potassium hydroxide and sodium hydrogen, and a combination thereof; and the organic base is selected from the group consisting of N,N-dimethylaminopyridine, triethylamine, diisopropylethylamine, tributylamine, potassium tert-butoxide, and a combination thereof.

In some embodiments, a molar ratio of the 4-chloropyrimidine derivative (II) to the biphenyl derivative (III) to the base is 1:1-1.5:1.5-3.

In some embodiments, the molar ratio of the 4-chloropyrimidine derivative (II) to the biphenyl derivative (III) to the base is 1:1.1:2.5.

In some embodiments, the reaction is performed at 30-100° C. for 4-10 h.

In a third aspect, the disclosure provides a pharmaceutically-acceptable salt and a derivative of the biphenyl-containing diarylpyrimido compound and a pharmaceutically acceptable prodrug, wherein the pharmaceutically-acceptable salt is selected from the group consisting of hydrochloride, hydrobromide, sulfate, phosphate, acetate, mesylate, tosylate, tartrate, citrate, fumarate and malate.

In a fourth aspect, the disclosure provides a pharmaceutical composition for treating AIDS, comprising: the biphenyl-containing diarylpyrimido compound or the pharmaceutically-acceptable salt as an active ingredient, and a pharmaceutically-acceptable carrier.

In a fifth aspect, the disclosure provides a method for preparing the pharmaceutical composition, comprising: using the biphenyl-containing diarylpyrimido compound or the pharmaceutically-acceptable salt thereof as an active ingredient to prepare the pharmaceutical composition.

In a sixth aspect, the disclosure provides a method of treating AIDS in a patient in need thereof, comprising: administering a therapeutically effective amount of the pharmaceutical composition to the patient.

In a seventh aspect, the disclosure also provides hydrates, solvates, polymorphs, codrugs, co-crystals, prodrugs, tautomers, racemates, enantiomers, diastereomers and derivatives of the above biphenyl-containing diarylpyrimido compound, and a mixture thereof.

Based on the binding mechanism between the biphenyl-containing diarylpyrimido compounds and HIV reverse transcriptase, the disclosure introduces other unsaturated or saturated cyclic structures into the pyrimidine ring by computer-aided drug design, which enhances the non-polar interaction between the compound and the amino acid residues V179 and E138 in the binding pocket. Moreover, the biphenyl structure on the left wing can go deep into the binding pocket, which strengthens the binding with the highly conserved amino acid residues Phe227 and Trp229, further improving the biological activity of the target compound against the drug-resistant HIV strains. The in vitro potency of the compound of the invention against HIV-1 is investigated in the cellular level, and the results demonstrate that the compound (I) has strong potency against HIV-1 and low cytotoxicity.

DETAILED DESCRIPTION OF EMBODIMENTS

In order to render the technical solutions, features, objects and beneficial effects of the invention clearer, the invention will be described below in detail in conjunction with embodiments. It should be understood that these embodiments are merely illustrative of the invention, and are not intended to limit the invention.

Detailed description will be made below to the biphenyl-containing diarylpyrimido compound according to the first aspect, the preparation method of the biphenyl-containing diarylpyrimido compound according to the second aspect, the pharmaceutically-acceptable salt of the biphenyl-containing diarylpyrimido compound according to the third aspect, the pharmaceutical composition according to the fourth aspect, the preparation method of the pharmaceutical composition in the fifth aspect and the method for treating AIDS in the sixth aspect.

The biphenyl-containing diarylpyrimido compound according to the first aspect has the following structural formula:

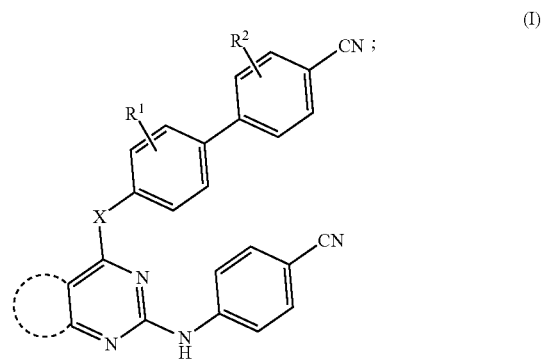

where $R^1$ and $R^2$ are independently selected from the group consisting of hydrogen, cyano, nitro, hydroxyl, halogen, amino, $C_3$-$C_6$ cycloalkoxy, $C_3$-$C_6$ cycloalkylamino, substituted $C_1$-$C_6$ alkyl, substituted $C_2$-$C_6$ alkenyl, substituted $C_2$-$C_6$ alkynyl, $C_1$-$C_6$ alkoxy, carboxyl, ester group, amido and sulfonamido;

X is selected from the group consisting of —CH$_2$—, —NH—, —O—, —S—, —S(O)— and —S(O)$_2$—; and ◌ is selected from the group consisting of unsubstituted and substituted benzene ring; thiophene, thiazole, pyrrole, pyrazole, pyran, imidazole, oxazole, isoxazole, pyrazolone, furan, pyridine, azine and an oxide thereof; cyclopentadiene; tetrahydrothiophene; sulphoxide; sulfone; tetrahydrofuran; and substituted cycloalkane.

Based on the binding mechanism between the biphenyl-containing diarylpyrimido compounds and HIV reverse transcriptase, the disclosure introduces other unsaturated or saturated cyclic structures into the pyrimidine ring by computer-aided drug design, which enhances the non-polar interaction between the compound and the amino acid residues V179 and E138 in the binding pocket. Moreover, the biphenyl structure on the left wing can go deep into the binding pocket, which strengthens the binding with the highly conserved amino acid residues Phe227 and Trp229, further improving the biological activity of the target compound against the drug-resistant HIV strains.

The biphenyl-containing diarylpyrimido compound according to the second aspect is prepared through steps of:

reacting a 4-chloropyrimidine derivative (II) with a biphenyl derivative (III) in a solvent in the presence of a base to obtain the compound (I), as shown in the following scheme:

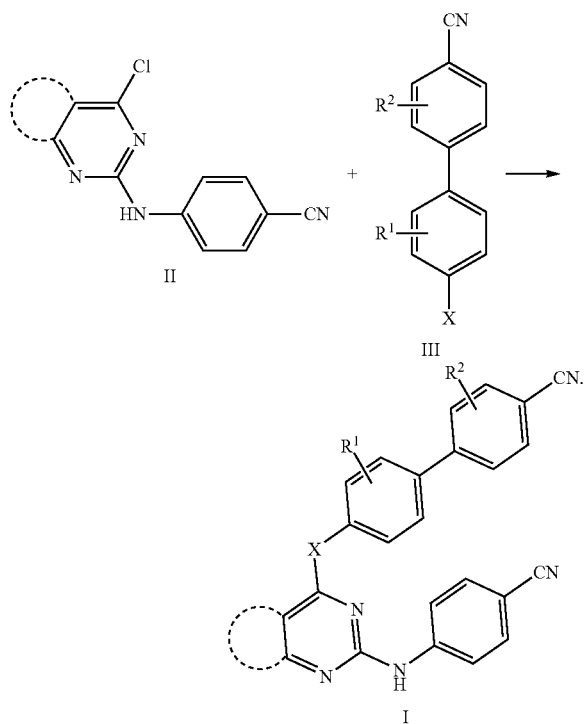

In some embodiments, the solvent is selected from the group consisting of acetone, acetonitrile, toluene, dichloromethane, tetrahydrofuran, N,N-dimethylformamide, N,N-dimethylacetamide, ethanol, isopropanol, n-butanol, isobutanol and a combination thereof.

In some embodiments, the base is an inorganic base or an organic base; where the inorganic base is selected from the group consisting of sodium carbonate, potassium carbonate, cesium carbonate, sodium hydroxide, potassium hydroxide and sodium hydrogen, and a combination thereof; and the organic base is selected from the group consisting of N,N-dimethylaminopyridine, triethylamine, diisopropylethylamine, tributylamine, potassium tert-butoxide, and a combination thereof.

In some embodiments, a molar ratio of the 4-chloropyrimidine derivative (II) to the biphenyl derivative (III) to the base is 1:1-1.5:1.5-3.

In some embodiments, a molar ratio of the 4-chloropyrimidine derivative (II) to the biphenyl derivative (III) to the base is 1:1.1:2.5.

In some embodiments, the reaction is performed at 30-100° C. for 4-10 h.

It has been confirmed through extensive experimental researches that the conversion rate, selectivity and yield of the preparation method are significantly improved under the above-mentioned reaction conditions.

In some embodiments, the separation and purification of the biphenyl-containing diarylpyrimido compound described herein can be performed by any suitable method, such as filtration, extraction, crystallization, column chromatography, thin layer chromatography, thick layer chromatography, preparative low pressure and high pressure liquid chromatography, and a combination thereof. Reference can be made to the following specific examples for the detailed illustration of separation and purification methods, and other feasible separation or purification methods can also be used.

The pharmaceutically-acceptable salt of the biphenyl-containing diarylpyrimido compound according to the third aspect is selected from the group consisting of hydrochloride, hydrobromide, sulfate, phosphate, acetate, mesylate, tosylate, tartrate, citrate, fumarate and malate.

The pharmaceutically-acceptable salts can be exemplarily prepared as follows. The compound of formula (I) is dissolved in an excess acidic aqueous solution (such as hydrochloric acid, hydrobromic acid, sulfuric acid, phosphoric acid, acetic acid, methanesulfonic acid, p-toluenesulfonic acid, tartaric acid, citric acid, fumaric acid and malic acid), to which an organic solvent that is miscible with water (such as methanol, ethanol, acetone and acetonitrile) is added, and the resulting salt spontaneously precipitates out of the solution.

The pharmaceutical composition according to the fourth aspect for treating AIDS includes the biphenyl-containing diarylpyrimido compound according to the first aspect or the pharmaceutically-acceptable salt according to the third aspect, and a pharmaceutically-acceptable carrier.

In some embodiments, the pharmaceutically-acceptable carrier is a conventional drug carrier, such as diluents, excipients, fillers, binders, wetting agents, disintegrants, absorption enhancers, surfactants, adsorption carriers, lubricants, dissolving agents, dissolution aids, coloring agents, deodorants, stabilizers, emulsifiers, adsorption enhancers, pH regulator, antiseptics and antioxidants. The fillers include, but are not limited to: starch, powdered sugar, calcium phosphate, dextrin, microcrystalline cellulose, lactose, pregelatinized starch and mannitol; the binders include, but are not limited to: sodium carboxymethyl cellulose, PVP-K30, hydroxypropyl cellulose, starch slurry, methyl cellulose, ethyl cellulose, hydroxypropyl methyl cellulose and gelatinized starch; the disintegrants include, but are not limited to: dry starch, crospovidone, croscarmellose sodium, sodium carboxymethyl starch and low-substituted hydroxypropyl cellulose; the lubricants include, but are not limited to: magnesium stearate, talcum powder, sodium dodecyl sulfate and micronized silica gel.

The pharmaceutical composition can be prepared by a conventional method into various dosage forms, such as dispersions, suspensions, tablets, pills, powders, suppositories, pulvis, fine granules, granules, syrups, electuaries, capsules, sprays, sustained-release preparations, injections, pastilles, inhalants, ointments, eye drops, nose drops, ear drops and patches. The pharmaceutical composition can also be used as an active ingredient and mixed with one or more pharmaceutically-acceptable carriers or drugs to prepare a product of the desired dosage form.

The method in the sixth aspect for treating AIDS in a patient in need thereof includes: administering a therapeutically effective amount of the pharmaceutical composition according to the fourth aspect to the patient. The in vitro activity of the compounds (I) against HIV-1 in the cellular level is evaluated, and the results show that the compound (I) of the invention has significant anti-HIV-1 activity and lower cytotoxicity.

The subjects to which the pharmaceutical composition according to the fourth aspect is administered include animals, preferably mammals, and more preferably humans. The treatment includes (i) prevention of diseases; (ii) suppression of the progression of the diseases; (iii) alleviation of the diseases; and (iv) alleviation of symptoms caused by the diseases.

The pharmaceutical composition according to the fourth aspect may be administered to the subjects (such as mammals including humans) in need of prevention and/or treatment by oral administration (such as in the form of powders, tablets, coated tablets, capsules, microcapsules, solutions, suspensions or emulsions), rectal administration (such as in the form of suppositories), parenteral administration (such as intravenous, intramuscular, subcutaneous or intraperitoneal injection of the composition, and infusion of the composition), respiratory administration (such as inhalation and insufflations of liquid or powder), transdermal administration (such as in the form of patches) or topical administration (such as in the form of creams, ointments and patches).

The liquid formulations acceptable for the parenteral administration are sterile isotonic solutions, which may contain, in addition to the solvent, certain auxiliaries to control the pH and preserve the composition. When the soft pharmaceutical composition is used as a suppository, the active ingredient (i.e., the biphenyl-containing diarylpyrimido compound according to the first aspect) is uniformly dispersed in a carrier (such as polyethylene glycol and cocoa butter).

The "therapeutically effective amount" refers to an amount at which the pharmaceutical composition applied can effectively treat, alleviate or prevent a disease or condition of interest in a subject in need thereof. The therapeutically effective amount of the pharmaceutical composition can vary within a wide range, and in the practical application, it should be determined according to the conditions of the subject, the status of the target disease, the pain severity and the administration route. For example, 25-100 mg of the biphenyl-containing diarylpyrimido compound or corresponding amount of its pharmaceutically-acceptable salt can be orally administered to an adult daily. The daily dose of the composition can be administered in a single administration or in multiple administrations.

The pharmaceutical composition can be administered simultaneously or sequentially in combination with one or more other active agents, such as antiviral agents, antibiotics and anti-inflammatory drugs.

In a seventh aspect, the disclosure provides hydrates, solvates, polymorphs, codrugs and cocrystals prodrugs, tautomers, racemates, enantiomers, diastereomers, derivatives of the biphenyl-containing diarylpyrimido compounds, and a combination thereof.

The following embodiments exemplarily illustrate the preparation of various target compounds from raw materials varying in substituent using the method according to the second aspect, and the invention is not limited to these embodiments.

Specifically, the biphenyl-containing diarylpyrimido compound (I) is prepared as follows.

Compound (III) and a base are added to a solvent and stirred for 30 min. Then the reaction mixture is added with compound (II) and stirred at 30-100° C. for 4-10 h. After the raw materials are completely consumed, as monitored by thin layer chromatography (TLC), the reaction mixture is poured into ethyl acetate. Then the reaction mixture is washed with water and saturated sodium chloride solution in turn. The organic phase is collected, dried with anhydrous sodium sulfate overnight, and then filtered. The filtrate is concentrated and recrystallized with ethyl acetate and petroleum ether to give the target product (I).

Example 1 Preparation of Biphenyl-Containing Diarylpyrimido Compound (Ia)

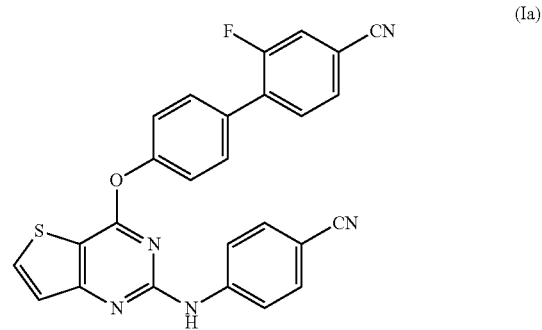 [SMILES: N#Cc1ccc(Nc2nc(Oc3ccc(-c4ccc(C#N)cc4F)cc3)c3sccc3n2)cc1]

(Ia)

0.35 mmol of 2-fluoro-4'-hydroxy-[1,1'-biphenyl]-4-carbonitrile and 0.88 mmol of potassium carbonate were added to 3 mL of N,N-dimethylformamide at room temperature. The reaction mixture was stirred for 30 min, then added with 0.35 mmol of 4-((4-chlorothieno[3,2-d]pyrimidin-2-yl)amino)benzonitrile and stirred at 80° C. for 9 h. After the raw materials were monitored by TLC to be completely consumed, the reaction mixture was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ia) (85% yield; mp: 272.5-273.6° C.).

¹H NMR (400 MHz, CF₃COOD, CDCl₃) δ: 8.44 (d, J=7.1 Hz, 1H), 7.76 (d, J=8.2 Hz, 2H), 7.72-7.63 (m, 3H), 7.48 (d, J=8.7 Hz, 2H), 7.41 (d, J=8.7 Hz, 2H), 7.35 (d, J=8.6 Hz, 2H), 6.91 (d, J=7.1 Hz, 1H).

¹³C NMR (101 MHz, CF₃COOD, CDCl₃) δ: 172.81, 159.21, 152.38, 151.78, 148.00, 139.75, 133.30, 131.69, 131.65, 130.92, 130.89, 129.09, 129.05, 121.78, 121.38, 120.69, 120.43, 118.43, 112.78, 109.96, 107.38, 101.57.

LCMS (ESI) m/z C₂₆H₁₄FN₅OS: calcd 463.09, found 464.31 [M+H]⁺.

Example 2 Preparation of Biphenyl-Containing Diarylpyrimido Compound (Ib)

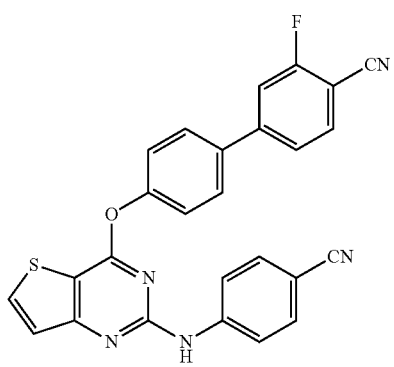

(Ib)

0.35 mmol of 3-fluoro-4'-hydroxy-[1,1'-biphenyl]-4-carbonitrile and 0.80 mmol of cesium carbonate were added to 3 mL of acetone at room temperature. The reaction mixture was stirred for 30 min, then added with 0.34 mmol of 4-((4-chlorothieno[3,2-d]pyrimidin-2-yl)amino)benzonitrile and stirred at 30° C. for 9 h. After the raw materials were monitored by TCL to be completely consumed, the reaction mixture was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ib) (92% yield; mp: 258.8-260.3° C.).

¹H NMR (400 MHz, CF₃COOD, CDCl₃) δ: 8.43 (d, J=5.4 Hz, 1H), 7.96 (d, J=8.2 Hz, 2H), 7.84 (d, J=7.9 Hz, 2H), 7.74 (t, J=8.5 Hz, 1H), 7.59-7.52 (m, 5H), 7.31 (t, J=8.1 Hz, 2H).

¹³C NMR (101 MHz, CF₃COOD, CDCl₃) δ: 172.84, 164.05, 152.40, 152.22, 147.97, 139.82, 137.48, 134.40, 133.20, 129.03, 123.43, 123.40, 122.22, 121.42, 118.44, 114.97, 114.76, 112.80, 109.98, 107.32, 101.59.

LCMS (ESI) m/z C₂₆H₁₄FN₅OS: calcd 463.09, found 464.50 [M+H]⁺.

Example 3 Preparation of Biphenyl-Containing Diarylpyrimido Compound (Ic)

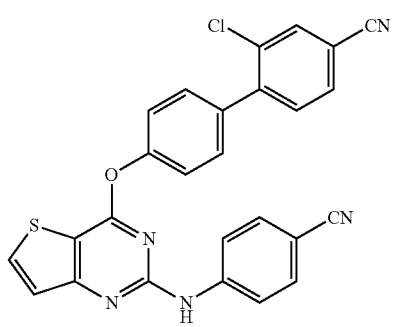

(Ic)

0.35 mmol of 2-chloro-4'-hydroxy-[1,1'-biphenyl]-4-carbonitrile and 0.82 mmol potassium carbonate were added to 3 mL of N,N-dimethylformamide at room temperature. The reaction mixture was stirred for 50 min, then added with 0.33 mmol of 4-((4-chlorothieno[3,2-d]pyrimidin-2-yl)amino)benzonitrile and stirred at 80° C. for 5 h. After the raw materials were monitored by TLC to be completely consumed, the reaction mixture was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ic) (74% yield; mp: >300° C.).

¹H NMR (400 MHz, CF₃COOD, CDCl₃) δ: 8.45 (d, J=7.1 Hz, 1H), 7.96 (s, 1H), 7.78 (d, J=9.2 Hz, 1H), 7.67 (d, J=8.5 Hz, 2H), 7.57 (d, J=8.0 Hz, 1H), 7.51 (d, J=8.8 Hz, 2H), 7.44 (d, J=8.8 Hz, 2H), 7.34 (d, J=8.5 Hz, 2H), 6.90 (d, J=7.1 Hz, 1H).

¹³C NMR (101 MHz, CF₃COOD, CDCl₃) δ: 172.79, 152.44, 151.53, 147.98, 144.54, 139.79, 136.99, 134.01, 133.66, 133.39, 131.97, 131.12, 131.04, 121.36, 118.43, 112.78, 111.60, 109.96, 107.35, 101.63.

LCMS (ESI) m/z C₂₆H₁₄ClN₅OS: calcd 479.06, found 480.33 [M+H]⁺.

Example 4 Preparation of Biphenyl-Containing Diarylpyrimido Compound (Id)

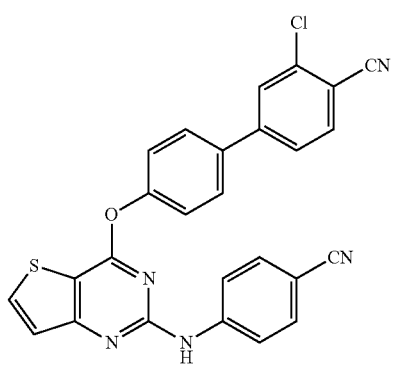

(Id)

0.35 mmol of 3-chloro-4'-hydroxy-[1,1'-biphenyl]-4-carbonitrile and 0.76 mmol of sodium carbonate were added to 3 mL of N,N-dimethylformamide at room temperature. The reaction mixture was stirred for 30 min, then added with 0.35 mmol of 4-((4-chlorothieno[3,2-d]pyrimidin-2-yl)amino)benzonitrile and stirred at 60° C. for 6 h. After the raw materials were monitored by TLC to be completely consumed, the reaction mixture was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Id) (81% yield; mp: 246.3-247.7° C.).

$^1$H NMR (400 MHz, CF$_3$COOD, CDCl$_3$) δ: 8.45 (d, J=6.9 Hz, 1H), 7.91 (d, J=8.0 Hz, 1H), 7.85 (s, 1H), 7.81 (d, J=8.1 Hz, 2H), 7.71 (d, J=8.1 Hz, 1H), 7.43 (s, 4H), 7.38 (d, J=8.0 Hz, 2H), 6.90 (d, J=6.7 Hz, 1H).

$^{13}$C NMR (101 MHz, CF$_3$COOD, CDCl$_3$) δ: 172.77, 152.39, 152.14, 148.08, 146.24, 139.82, 138.35, 137.43, 134.99, 133.23, 129.11, 128.53, 125.72, 122.25, 121.37, 118.43, 112.79, 111.03, 109.96, 107.38, 101.57.

LCMS (ESI) m/z C$_{26}$H$_{14}$ClN$_5$OS: calcd 479.06, found 502.34 [M+Na]$^+$.

Example 5 Preparation of Biphenyl-Containing Diarylpyrimido Compound (Ie)

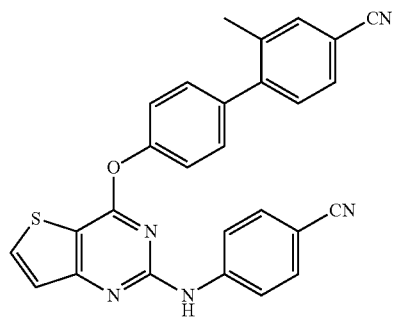

(Ie)

0.35 mmol of 4'-hydroxy-2-methyl-[1,1'-biphenyl]-4-carbonitrile and 0.88 mmol of sodium hydroxide were added to 3 mL of N,N-dimethylformamide at room temperature. The reaction mixture was stirred for 30 min, then added with 0.34 mmol of 4-((4-chlorothieno[3,2-d]pyrimidin-2-yl)amino)benzonitrile and stirred at 90° C. for 8 h. After the raw materials were monitored by TLC to be completely consumed, the reaction mixture was poured into 15 mL of ethyl acetate. Then the reaction mixture was washed with water three times each for 6 mL and saturated sodium chloride solution twice each for 6 mL. The organic phase was collected, dried through anhydrous sodium sulfate overnight, and then filtered. The resulting filtrate was concentrated and recrystallized with ethyl acetate and petroleum ether to give a white powdery solid as the target product (Ie) (82% yield; mp: 278.4-279.5° C.).

1H NMR (400 MHz, CF$_3$COOD, CDCl$_3$) δ: 8.45 (d, J=7.0 Hz, 1H), 7.76 (s, 1H), 7.73 (d, J=7.8 Hz, 1H), 7.57-7.51 (m, 6H), 7.46 (d, J=7.8 Hz, 1H), 7.36 (d, J=8.4 Hz, 2H), 6.92 (d, J=6.9 Hz, 1H), 2.42 (s, 3H). $^{13}$C NMR (101 MHz, CF$_3$COOD, CDCl$_3$) δ: 173.00, 152.52, 151.03, 147.69, 146.03, 139.86, 139.58, 137.19, 134.42, 133.23, 130.53, 130.36, 130.05, 121.58, 121.21, 118.38, 112.75, 109.93, 101.64, 19.41.

LCMS (ESI) m/z C$_{27}$H$_{17}$N$_5$OS: calcd 459.12, found 460.40 [M+H]$^+$.

Example 6 Preparation of Biphenyl-Containing Diarylpyrimido Compound (If)

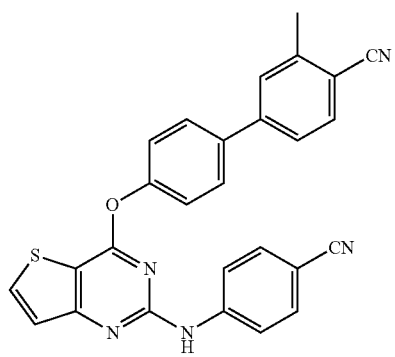

(If)

0.35 mmol of 4'-hydroxy-3-methyl-[1,1'-biphenyl]-4-carbonitrile and 0.88 mmol of potassium hydroxide were added to 3 mL of N,N-dimethylformamide at room temperature. The reaction mixture was stirred for 30 min, then added with 0.32 mmol of 4-((4-chlorothieno[3,2-d]pyrimidin-2-yl)amino)benzonitrile and stirred at 100° C. for 10 h. After the raw materials were monitored by TLC to be completely consumed, the reaction mixture was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (If) (75% yield; mp: 256.5-257.9° C.).

$^1$H NMR (400 MHz, DMSO-d$_6$) δ: 10.07 (s, 1H), 8.37 (d, J=5.2 Hz, 1H), 7.95 (d, J=7.6 Hz, 2H), 7.86 (d, J=8.3 Hz, 2H), 7.63 (d, J=7.6 Hz, 2H), 7.56 (d, J=8.2 Hz, 2H), 7.46 (d, J=5.2 Hz, 1H), 7.39 (d, J=8.6 Hz, 2H), 7.32 (d, J=8.3 Hz, 1H), 2.30 (s, 3H).

$^{13}$C NMR (101 MHz, CF$_3$COOD, CDCl$_3$) δ: 166.81, 151.58, 151.16, 150.35, 146.17, 142.62, 140.46, 139.51, 138.20, 133.14, 132.78, 131.04, 129.97, 123.29, 121.49, 119.06, 118.47, 117.45, 112.82, 111.73, 110.00, 109.69, 106.92, 19.88.

LCMS (ESI) m/z C$_{27}$H$_{17}$N$_5$OS: calcd 459.12, found 460.28 [M+H]$^+$.

Example 7 Preparation of Biphenyl-Containing Diarylpyrimido Compound (Ig)

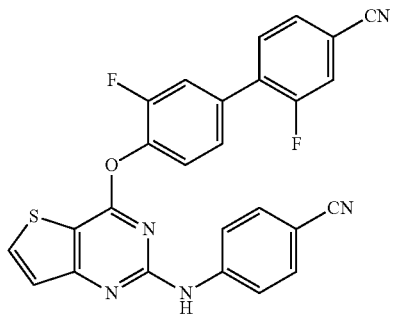

(Ig)

0.35 mmol of 2,3'-difluoro-4'-hydroxy-[1,1'-biphenyl]-4-carbonitrile and 0.88 mmol of potassium carbonate were added to 3 mL of N,N-dimethylformamide at room temperature. The reaction mixture was stirred for 30 min, then added with 0.33 mmol of 4-((4-chlorothieno[3,2-d]pyrimidin-2-yl)amino)benzonitrile and stirred at 80° C. for 9 h. After the raw materials were monitored by TLC to be completely consumed, the reaction mixture was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ig) (67% yield; mp: 295.3-297.0° C.).

$^1$H NMR (400 MHz, CF$_3$COOD, CDCl$_3$) δ: 8.41 (d, J=5.4 Hz, 1H), 7.75-7.68 (m, 3H), 7.59 (d, J=10.5 Hz, 1H), 7.58-7.51 (m, 5H), 7.45 (d, J=8.7 Hz, 2H).

$^{13}$C NMR (101 MHz, CF$_3$COOD, CDCl$_3$) δ: 165.84, 159.13, 153.51, 151.76, 150.86, 143.18, 140.09, 139.02, 138.89, 134.99, 133.24, 131.55, 129.14, 125.86, 123.66, 121.83, 120.54, 118.46, 117.49, 112.82, 111.23, 109.99, 107.30.

LCMS (ESI) m/z C$_{26}$H$_{13}$F$_2$N$_5$OS: calcd 481.08, found 482.29 [M+H]$^+$.

Example 8 Preparation of Biphenyl-Containing Diarylpyrimido Compound (Ih)

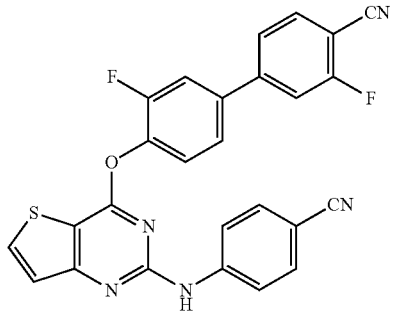

(Ih)

0.35 mmol of 3,3'-difluoro-4'-hydroxy-[1,1'-biphenyl]-4-carbonitrile and 0.90 mmol of sodium hydride were added to 3 mL of N,N-dimethylformamide at room temperature. The reaction mixture was stirred for 30 min, added with 0.34 mmol of 4-((4-chlorothieno[3,2-d]pyrimidin-2-yl)amino)benzonitrile and stirred at 80° C. for 9 h. After the raw materials were monitored by TLC to be completely consumed, the reaction mixture was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ih) (83% yield; mp: >300° C.).

$^1$H NMR (400 MHz, CF$_3$COOD, CDCl$_3$) δ: 8.42 (d, J=5.4 Hz, 1H), 7.94-7.87 (m, 1H), 7.66-7.52 (m, 7H), 7.45 (s, 3H).

$^{13}$C NMR (101 MHz, CF$_3$COOD, CDCl$_3$) δ: 165.80, 164.02, 154.01, 151.74, 150.90, 143.30, 140.16, 134.63, 133.12, 124.18, 124.02, 123.39, 121.84, 118.47, 117.51, 116.02, 115.83, 115.06, 114.86, 112.82, 111.27, 110.00, 107.26, 99.81, 99.65.

LCMS (ESI) m/z C$_{26}$H$_{13}$F$_2$N$_5$OS: calcd 481.08, found 504.36 [M+Na]$^+$.

Example 9 Preparation of Biphenyl-Containing Diarylpyrimido Compound (Ii)

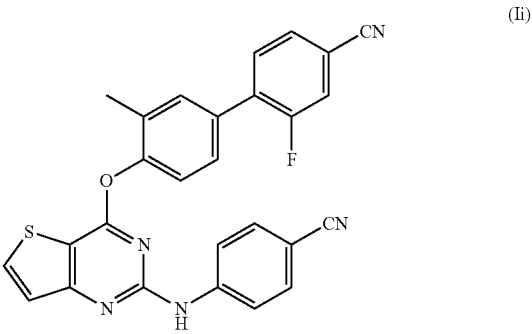 [SMILES: Cc1cc(-c2ccc(C#N)cc2F)ccc1Oc1nc(Nc2ccc(C#N)cc2)nc2ccsc12]

(Ii)

0.35 mmol of 2-fluoro-4'-hydroxy-3'-methyl-[1,1'-biphenyl]-4-carbonitrile and 0.88 mmol of N,N-dimethylaminopyridine were added to 3 mL of isobutanol at room temperature. The reaction mixture was stirred for 30 min, then added with 0.35 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried through anhydrous sodium sulfate overnight, and then filtered. The resulting filtrate was concentrated and recrystallized with ethyl acetate and petroleum ether to give a white powdery solid as the target product (Ii) (89% yield; mp: 268.5-271.0° C.).

$^1$H NMR (400 MHz, CF$_3$COOD, CDCl$_3$) δ: 8.38 (d, J=5.4 Hz, 1H), 7.70 (d, J=5.5 Hz, 2H), 7.67-7.60 (m, 3H), 7.54 (d, J=5.4 Hz, 1H), 7.46 (d, J=8.7 Hz, 2H), 7.41-7.36 (m, 3H), 2.33 (s, 3H).

$^{13}$C NMR (101 MHz, CF$_3$COOD, CDCl$_3$) δ: 166.75, 159.54, 151.91, 150.99, 143.02, 140.61, 133.79, 132.78, 132.07, 131.31, 129.37, 128.67, 122.33, 121.50, 120.99, 118.79, 117.94, 113.14, 111.72, 110.32, 107.26, 15.90.

LCMS (ESI) m/z $C_{27}H_{16}FN_5OS$: calcd 477.11, found 500.33 $[M+Na]^+$.

Example 10 Preparation of Biphenyl-Containing Diarylpyrimido Compound (Ij)

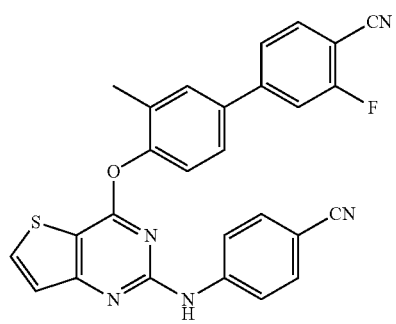

0.35 mmol of 3-fluoro-4'-hydroxy-3'-methyl-[1,1'-biphenyl]-4-carbonitrile and 0.93 mmol of triethylamine were added to 3 mL of n-butanol at room temperature. The reaction mixture was stirred for 30 min, then added with 0.34 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ij) (81% yield; mp: 299.3-300.2° C.).

$^1$H NMR (400 MHz, $CF_3COOD$, $CDCl_3$) δ: 8.43 (d, J=5.4 Hz, 1H), 7.91 (t, J=7.2 Hz, 1H), 7.75-7.67 (m, 3H), 7.62 (d, J=9.9 Hz, 1H), 7.57 (d, J=5.3 Hz, 1H), 7.49-7.37 (m, 5H), 2.38 (s, 3H).

$^{13}$C NMR (101 MHz, $CF_3COOD$, $CDCl_3$) δ: 166.47, 159.08, 165.38, 162.79, 151.60, 151.15, 150.55, 142.85, 140.38, 137.70, 133.16, 130.67, 126.42, 121.30, 118.49, 117.51, 114.94, 114.74, 112.84, 111.40, 110.02, 106.88, 98.74, 15.42.

LCMS (ESI) m/z $C_{27}H_{16}FN_5OS$: calcd 477.11, found 478.44 $[M+H]^+$.

Example 11 Preparation of Biphenyl-Containing Diarylpyrimido Compound (Ik)

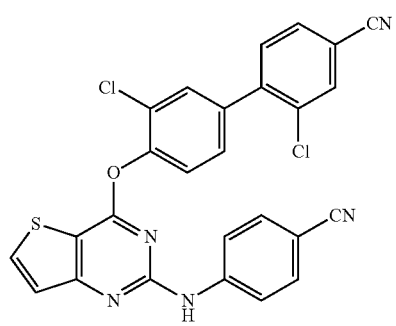

0.35 mmol of 2,3'-dichloro-4'-hydroxy-[1,1'-biphenyl]-4-carbonitrile and 0.88 mmol of diisopropyl ethylamine were added to 3 mL of isopropanol at room temperature. The reaction mixture was stirred for 30 min, then added with 0.34 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ik) (90% yield; mp: 298.4-300.9° C.).

$^1$H NMR (400 MHz, $CF_3COOD$, $CDCl_3$) δ: 8.52 (d, J=7.0 Hz, 1H), 7.98 (s, 1H), 7.81 (d, J=8.0 Hz, 1H), 7.74 (s, 1H), 7.61-7.50 (m, 4H), 7.46-7.38 (m, 3H), 6.98 (d, J=7.0 Hz, 1H).

$^{13}$C NMR (101 MHz, $CF_3COOD$, $CDCl_3$) δ: 172.01, 152.51, 148.51, 147.72, 143.29, 139.65, 138.24, 134.07, 133.61, 133.34, 131.84, 131.41, 131.14, 129.41, 126.86, 123.02, 121.66, 118.45, 112.80, 112.09, 109.98, 107.52, 101.30.

Example 12 Preparation of Biphenyl-Containing Diarylpyrimido Compound (Il)

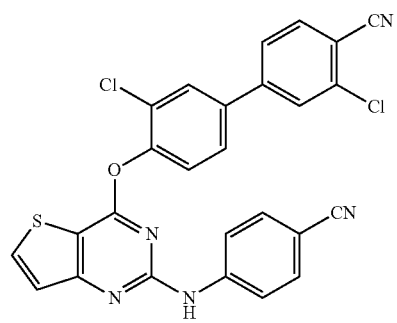

0.35 mmol of 3,3'-dichloro-4'-hydroxy-[1,1'-biphenyl]-4-carbonitrile and 0.88 mmol of tributylamine were added to 3 mL of N,N-dimethylformamide at room temperature. The reaction mixture was stirred for 30 min, then added with 0.34 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Il) (75% yield; mp: 245.6-247.3° C.).

$^1$H NMR (400 MHz, $CF_3COOD$, $CDCl_3$) δ: 8.53 (d, J=7.0 Hz, 1H), 7.93 (d, J=8.1 Hz, 1H), 7.86 (d, J=1.8 Hz, 1H), 7.83 (s, 1H), 7.72-7.66 (m, 2H), 7.51-7.44 (m, 3H), 7.38 (d, J=8.8 Hz, 2H), 6.97 (d, J=7.0 Hz, 1H).

$^{13}$C NMR (101 MHz, $CF_3COOD$, $CDCl_3$) δ: 171.96, 152.45, 148.71, 148.23, 144.91, 139.69, 138.79, 138.53, 135.13, 133.15, 129.52, 128.52, 127.88, 127.30, 125.71, 123.92, 121.62, 118.45, 112.80, 111.72, 109.98, 107.56, 101.22.

Example 13 Preparation of Biphenyl-Containing Diarylpyrimido Compound (Im)

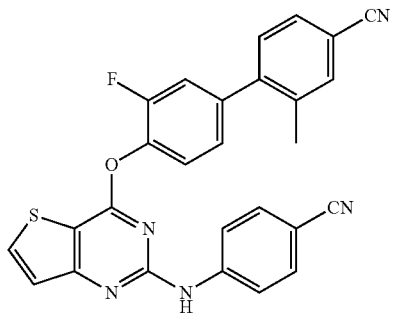

(Im)

0.35 mmol of 3'-fluoro-4'-hydroxy-2-methyl-[1,1'-biphenyl]-4-carbonitrile and 0.88 mmol of potassium tert-butoxide were added to 3 mL of acetonitrile at room temperature. The reaction mixture was stirred for 30 min, then added with 0.35 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Im) (86% yield; mp: 275.2-276.8° C.).

$^1$H NMR (400 MHz, CF$_3$COOD, CDCl$_3$) δ: 8.40 (d, J=5.4 Hz, 1H), 7.76-7.69 (m, 2H), 7.57-7.46 (m, 6H), 7.42 (d, J=7.9 Hz, 1H), 7.39-7.25 (m, 2H), 2.39 (s, 3H).

$^{13}$C NMR (101 MHz, CF$_3$COOD, CDCl$_3$) δ: 165.89, 153.26, 151.86, 150.79, 144.77, 143.18, 141.34, 140.15, 138.15, 138.02, 137.09, 133.17, 130.23, 125.71, 123.31, 122.04, 117.48, 112.88, 111.38, 110.05, 107.37, 19.61.

LCMS (ESI) m/z C$_{27}$H$_{16}$FN$_5$OS: calcd 477.11, found 478.32 [M+H]$^+$.

Example 14 Preparation of Biphenyl-Containing Diarylpyrimido Compound (In)

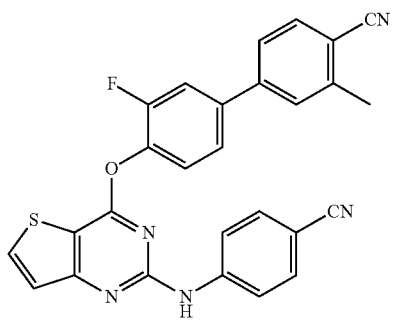

(In)

0.35 mmol of 3'-fluoro-4'-hydroxy-2-methyl-[1,1'-biphenyl]-4-carbonitrile and 0.88 mmol of potassium carbonate were added to 3 mL of toluene at room temperature. The reaction mixture was stirred for 30 min, then added with 0.35 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (In) (91% yield; mp: 252.5-254.2° C.).

$^1$H NMR (400 MHz, DMSO-d$_6$) δ: 10.12 (s, 1H, NH), 8.43 (d, J=5.3 Hz, 1H), 7.99-7.88 (m, 3H), 7.82-7.69 (m, 5H), 7.56-7.44 (m, 3H), 2.60 (s, 3H).

$^{13}$C NMR (101 MHz, DMSO-d$_6$) δ: 165.15, 163.48, 157.17, 155.93, 153.47, 145.24, 142.88, 142.82, 139.69, 138.55, 133.69, 133.13, 129.21, 125.67, 125.39, 124.53, 123.88, 119.91, 118.73, 118.38, 116.22, 116.03, 111.71, 108.92, 102.78, 20.53.

LCMS (ESI) m/z C$_{27}$H$_{16}$FN$_5$OS: calcd 477.11, found 478.32 [M+H]$^+$.

Example 15 Preparation of Biphenyl-Containing Diarylpyrimido Compound (Io)

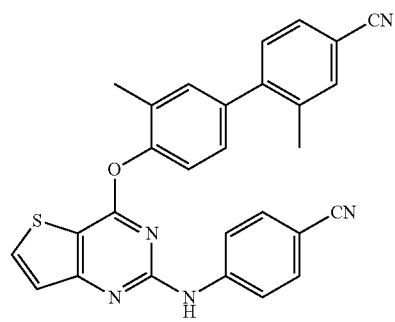

(Io)

0.35 mmol of 4'-hydroxy-2,3'-dimethyl-[1,1'-biphenyl]-4-carbonitrile and 0.88 mmol of potassium carbonate were added to 3 mL of dichloromethane at room temperature. The reaction mixture was stirred for 30 min, then added with 0.34 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Io) (88% yield; mp: 262.4-263.7° C.).

¹H NMR (400 MHz, CF₃COOD, CDCl₃) δ: 8.40 (d, J=5.4 Hz, 1H), 7.76 (s, 1H), 7.73 (d, J=8.0 Hz, 1H), 7.57-7.46 (m, 6H), 7.44-7.36 (m, 3H), 2.44 (s, 3H), 2.35 (s, 3H).

¹³C NMR (101 MHz, CF₃COOD, CDCl₃) δ: 166.62, 151.71, 150.39, 149.89, 146.26, 142.66, 140.43, 139.81, 137.22, 134.42, 133.22, 132.16, 130.60, 130.38, 130.02, 127.95, 121.52, 121.41, 118.45, 117.44, 112.81, 111.53, 109.99, 109.62, 106.90, 19.49, 15.26.

LCMS (ESI) m/z $C_{28}H_{19}N_5OS$: calcd 473.13, found 474.41 [M+H]⁺.

Example 16 Preparation of Biphenyl-Containing Diarylpyrimido Compound (Ip)

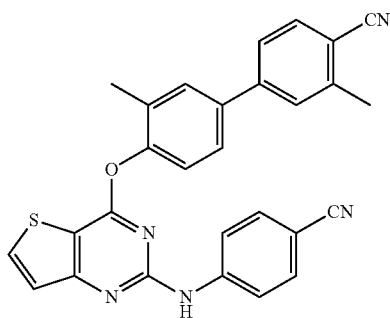

(Ip)

0.35 mmol of 4'-hydroxy-3,3'-dimethyl-[1,1'-biphenyl]-4-carbonitrile and 0.88 mmol of potassium carbonate were added to 3 mL of tetrahydrofuran at room temperature. The reaction mixture was stirred for 30 min, then added with 0.35 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ip) (92% yield; mp: 259.4-261.1° C.).

¹H NMR (400 MHz, CF₃COOD, CDCl₃) δ: 8.41 (d, J=5.4 Hz, 1H), 7.89 (d, J=8.0 Hz, 1H), 7.75-7.68 (m, 4H), 7.58 (d, J=5.4 Hz, 1H), 7.45 (s, 4H), 7.40 (d, J=8.3 Hz, 1H), 2.74 (s, 3H), 2.38 (s, 3H).

¹³C NMR (101 MHz, CF₃COOD, CDCl₃) δ: 166.61, 151.55, 150.67, 150.50, 145.13, 143.84, 142.58, 140.43, 139.18, 133.65, 133.17, 131.20, 130.70, 128.83, 126.48, 124.97, 122.19, 121.15, 118.39, 112.75, 109.93, 19.62, 15.32.

LCMS (ESI) m/z $C_{28}H_{19}N_5OS$: calcd 473.13, found 474.28 [M+H]⁺.

Example 17 Preparation of Biphenyl-Containing Diarylpyrimido Compound (Iq)

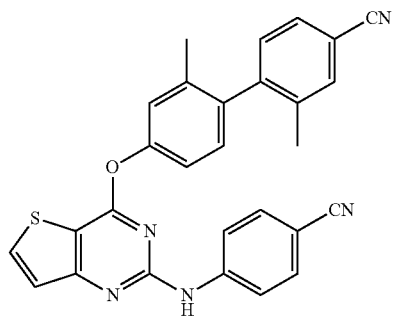

(Iq)

0.35 mmol of 4'-hydroxy-2,2'-dimethyl-[1,1'-biphenyl]-4-carbonitrile and 0.88 mmol of potassium carbonate were added to 3 mL of N,N-dimethylacetamide at room temperature. The reaction mixture was stirred for 30 min, then added with 0.34 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Iq) (86% yield; mp: 274.3-275.8° C.).

¹H NMR (400 MHz, CF₃COOD, CDCl₃) δ: 8.43 (d, J=7.1 Hz, 1H), 7.75 (s, 1H), 7.71 (d, J=7.9 Hz, 1H), 7.56 (s, 4H), 7.30 (dd, J=11.4, 8.1 Hz, 2H), 7.19 (s, 1H), 7.16 (d, J=8.2 Hz, 1H), 6.88 (d, J=7.1 Hz, 1H), 2.20 (s, 3H), 2.14 (s, 3H).

¹³C NMR (101 MHz, CF₃COOD, CDCl₃) δ: 172.87, 152.54, 150.88, 147.69, 146.01, 139.93, 139.07, 138.45, 137.82, 134.08, 133.26, 130.24, 130.18, 130.06, 122.51, 121.64, 118.53, 118.46, 115.63, 112.81, 109.99, 109.91, 107.37, 101.70, 19.25, 19.03.

LCMS (ESI) m/z $C_{28}H_{19}N_5OS$: calcd 473.13, found 474.34 [M+H]⁺.

Example 18 Preparation of Biphenyl-Containing Diarylpyrimido Compound (Ir)

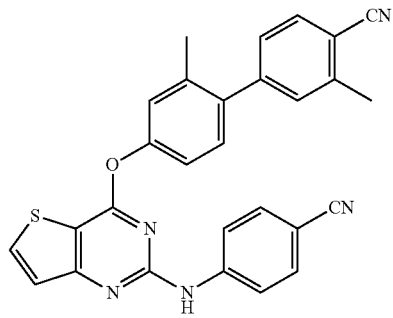

(Ir)

0.35 mmol of 4'-hydroxy-2,3'-dimethyl-[1,1'-biphenyl]-4-carbonitrile and 0.88 mmol of potassium carbonate were added to 3 mL of ethanol at room temperature. The reaction mixture was stirred for 30 min, then added with 0.35 mmol of 4-((4-chlorothieno[3,2-d]pyrimidin-2-yl)amino)benzonitrile and stirred at 80° C. for 9 h. After the raw materials were monitored by TLC to be completely consumed, the reaction solution was poured into 15 mL of ethyl acetate. Then the reaction mixture was washed with water three times each for 6 mL and saturated sodium chloride solution twice each for 6 mL. The organic phase was collected, dried with anhydrous sodium sulfate overnight, and then filtered. The resulting filtrate was concentrated and recrystallized with ethyl acetate and petroleum ether to give a white powdery solid as the target product (Ir) (71% yield; mp: 264.9-266.2° C.).

$^1$H NMR (400 MHz, $CF_3COOD$, $CDCl_3$) δ: 8.42 (d, J=7.1 Hz, 1H), 7.83 (d, J=7.9 Hz, 1H), 7.51 (s, 4H), 7.45-7.39 (m, 2H), 7.36 (d, J=8.0 Hz, 1H), 7.17 (d, J=7.2 Hz, 2H), 6.88 (d, J=7.1 Hz, 1H), 2.68 (s, 3H), 2.35 (s, 3H).

$^{13}$C NMR (101 MHz, $CF_3COOD$, $CDCl_3$) δ: 172.99, 152.38, 151.08, 147.75, 146.08, 143.29, 139.99, 139.59, 138.24, 133.21, 133.09, 131.02, 130.99, 127.14, 122.91, 121.44, 118.67, 118.44, 112.79, 107.25, 101.56, 19.85, 19.80.

LCMS (ESI) m/z $C_{28}H_{19}N_5OS$: calcd 473.13, found 474.41 $[M+H]^+$.

Experimental Example 1 Anti-HIV Biological Activity Test

The in vitro anti-HIV activity at the cellular level was determined by the Rega Institute for Medical Research, University of Katholleke, Belgium, in which the inhibitory activity of compounds Ia-Ir on HIV-infected MT-4 cells and cytotoxicity of compounds Ia-Ir were evaluated. The inhibitory activity was expressed by $EC_{50}$, i.e., the effective concentration of each compound required to protect 50% of MT-4 cells against viral cytopathicity, which was determined by MTT assay. The cytotoxicity test was performed in parallel with the anti-HIV activity test, and was expressed by $CC_{50}$, i.e., the cytotoxic concentration of each compound that reduced the normal uninfected MT-4 cell viability by 50%, which was also measured by MTT assay. Further, the selectivity index SI was calculated according to a ratio of $CC_{50}$ to $EC_{50}$.

Materials and Methods

The anti-HIV activity of each compound was evaluated according to the inhibition efficiency for the HIV-induced cytopathic effect in cells.

Cell: MT-4 cells.

Virus strains: HIV-1 IIIB and HIV-2 ROD.

Specifically, each compound was dissolved with DMSO or water, and diluted with a phosphate buffered solution at different dilution factors. $3×10^5$ MT-4 cells were separately pre-cultured in 100 μL of solutions of different concentrations of each compound at 37° C. for 1 h, to which 100 μL of a virus dilution was added. Then the cells were cultured at 37° C. for 1 h. After washed three times, the cells were suspended again in a culture medium with or without the compound, respectively, and cultured at 37° C. and 5% $CO_2$ for 7 d. The culture medium was accordingly replaced with a fresh culture medium with or without the compound on the third day after infection. Each treatment was performed in duplicate. The HIV-induced cytopathic effect was monitored daily with a reverse optical microscope. The significant cytopathic effect caused by HIV was generally observed on the fifth day after infection. The inhibitory effect of the compound was as assessed using the concentration ($CC_{50}$) at which the compound reached a 50% inhibitory effect on the HIV-induced cytopathic effect without direct toxicity to the cells. It should be noted that dimethyl sulfoxide (DMSO) was often employed to dissolve the compound with poor water solubility, but the specific concentration of DMSO should be generally less than 10% relative to water (the final concentration of DMSO in the MT-4 cell culture system should be less than 2%). Furthermore, since DMSO can affect the antiviral activity of the compound, the blank group should also be added with the same concentration of DMSO and test for the antiviral activity simultaneously. In addition, the final concentration of DMSO (1/1000) was much lower than the concentration required for HIV-1 to replicate in T cells.

Commercially-available drugs Nevirapine (NVP), Efavirenz (EFV) and Etravirine (ETR) were used as references, and the results of inhibitory activity of the target compounds Ia-Ir (Examples 1-18) against HIV were shown in Table 1.

TABLE 1

Anti-HIV activity and cytotoxicity of compounds 1-18 in MT-4 cells

| Example | HIV-1 (IIIB) $EC_{50}$ (μM)[b] | $CC_{50}$ (μM)[c] | SI (IIIB)[d] |
|---|---|---|---|
| 1 | 0.011 ± 0.008 | >53.98 | >4184 |
| 2 | 0.11 ± 0.077 | >269.92 | >2365 |
| 3 | 0.376 ± 0.103 | >260.92 | >700 |
| 4 | 0.075 ± 0.045 | >260.92 | >3434 |
| 5 | 0.070 ± 0.021 | >272.26 | >3860 |
| 6 | 0.074 ± 0.039 | >272.26 | >3706 |
| 7 | 0.139 ± 0.056 | 42.23 ± 11.72 | 302 |
| 8 | 4.095 ± 0.91 | >259.83 | >63 |
| 9 | 0.029 ± 0.005 | 9.47 ± 0.85 | 324 |
| 10 | 0.23 ± 0.143 | 46.02 ± 13.40 | 194 |
| 11 | 0.060 ± 0.027 | >243.65 | >4013 |
| 12 | 0.021 ± 0.010 | ≥20.21 | ≥963 |
| 13 | 0.065 ± 0.008 | 245.87 ± 53.67 | 3806 |
| 14 | 0.174 ± 0.094 | 35.25 ± 5.80 | 202 |
| 15 | 0.095 ± 0.054 | 152.07 ± 6.91 | 1606 |
| 16 | 0.146 ± 0.033 | 6.15 ± 0.42 | 42 |
| 17 | 0.014 ± 0.005 | 65.96 ± 4.5 | 4741 |
| 18 | 0.017 ± 0.012 | 264.19 ± 17.23 | 18564 |
| NVP | 0.293 ± 0.107 | >15.03 | >51 |
| EFV | 0.007 ± 0.005 | >6.34 | >863 |
| ETR | 0.006 ± 0.002 | >4.61 | >833 |

Notes:
[a] All data represent mean values of at least three separate experiments.
[b] $EC_{50}$: effective concentration required to protect 50% of cells against viral cytopathicity in MT-4 cells.
[c] $CC_{50}$: cytotoxic concentration of the compound that reduces the normal uninfected MT-4 cell viability by 50%.
[d] SI: selectivity index, ratio $CC_{50}/EC_{50}$ (WT).

It can be seen from Table 1 that the compounds of formula (I) generally exhibited strong anti-HIV-1 activity, which can further significantly inhibit the viral replication in HIV-1-infected MT-4 cells. Moreover, these compounds also had relatively low cytotoxicity and high selectivity index.

It should be noted that described above are merely preferred embodiments of the invention, which are not intended to limit the invention. Any modification and change made by those skilled in the art without departing from the spirit of the invention should fall within the scope of the invention defined by the appended claims.

What is claimed is:

1. A biphenyl-containing diarylpyrimido compound of formula (I):

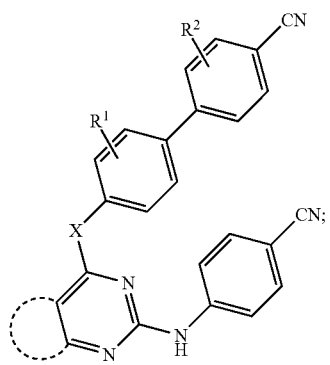

(I)

wherein:
R¹ is selected from the group consisting of hydrogen, cyano, nitro, hydroxyl, halogen, amino, $C_3$-$C_6$ cycloalkoxy, $C_3$-$C_6$ cycloalkylamino, substituted $C_1$-$C_6$ alkyl, substituted $C_2$-$C_6$ alkenyl, substituted $C_2$-$C_6$ alkynyl, $C_1$-$C_6$ alkoxy, carboxyl, ester group, amido and sulfonamido;

R² is selected from the group consisting of cyano, nitro, hydroxyl, halogen, amino, $C_3$-$C_6$ cycloalkoxy, $C_3$-$C_6$ cycloalkylamino, substituted $C_1$-$C_6$ alkyl, substituted $C_2$-$C_6$ alkenyl, substituted $C_2$-$C_6$ alkynyl, $C_1$-$C_6$ alkoxy, carboxyl, ester group, amido and sulfonamido;

X is selected from the group consisting of —$CH_2$—, —NH—, —O—, —S—, —S(O)— and —$S(O)_2$—; and

is selected from the group consisting of unsubstituted and substituted benzene ring; thiophene, thiazole, oxazole, isoxazole, pyrazolone, furan, pyridine, azine and an oxide thereof; cyclopentadiene; tetrahydrothiophene; sulphoxide; sulfone; tetrahydrofuran; and substituted cycloalkane.

2. The biphenyl-containing diarylpyrimido compound of claim 1, wherein the biphenyl-containing diarylpyrimido compound of formula (I) is prepared through steps of:
reacting a 4-chloropyrimidine derivative (II) with a biphenyl derivative (III) in a solvent in the presence of a base to produce the biphenyl-containing diarylpyrimido compound, as shown in the following scheme:

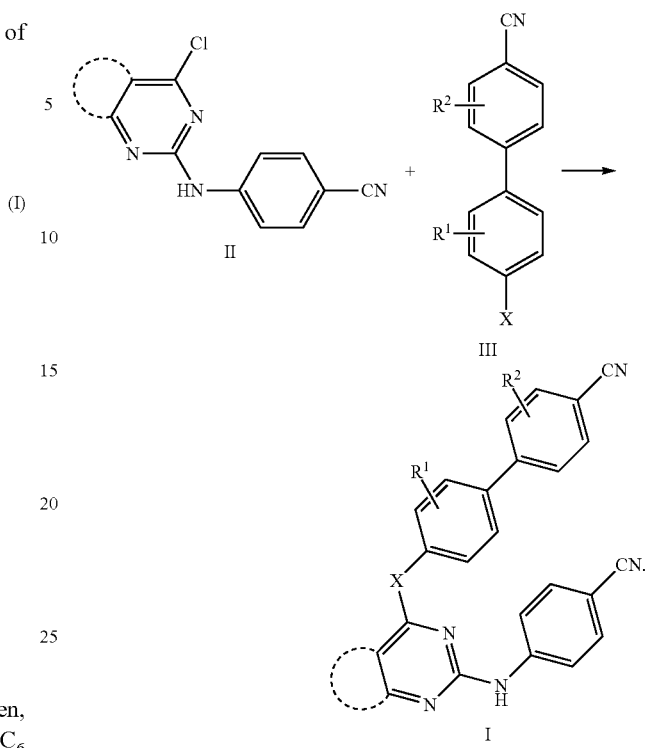

3. The biphenyl-containing diarylpyrimido compound of claim 2, wherein the solvent is selected from the group consisting of acetone, acetonitrile, toluene, dichloromethane, tetrahydrofuran, N,N-dimethylformamide, N,N-dimethylacetamide, ethanol, isopropanol, n-butanol and isobutanol, and a combination thereof.

4. The biphenyl-containing diarylpyrimido compound of claim 2, wherein the base is an inorganic base or an organic base;
wherein the inorganic base is selected from the group consisting of sodium carbonate, potassium carbonate, cesium carbonate, sodium hydroxide, potassium hydroxide and sodium hydrogen, and a combination thereof; and the organic base is selected from the group consisting of N,N-dimethylaminopyridine, triethylamine, diisopropylethylamine, tributylamine, potassium tert-butoxide, and a combination thereof.

5. The biphenyl-containing diarylpyrimido compound of claim 2, wherein a molar ratio of the 4-chloropyrimidine derivative (II) to the biphenyl derivative (III) to the base is 1:1-1.5:1.5-3.

6. The biphenyl-containing diarylpyrimido compound of claim 2, wherein a molar ratio of the 4-chloropyrimidine derivative (II) to the biphenyl derivative (III) to the base is 1:1.1:2.5.

7. The biphenyl-containing diarylpyrimido compound of claim 2, wherein the reaction is performed at 30-100° C. for 4-10 h.

8. A pharmaceutically-acceptable salt of the biphenyl-containing diarylpyrimido compound of claim 1, wherein the pharmaceutically-acceptable salt is selected from the group consisting of hydrochloride, hydrobromide, sulfate, phosphate, acetate, mesylate, tosylate, tartrate, citrate, fumarate and malate.

9. A pharmaceutical composition for treating acquired immunodeficiency syndrome (AIDS), comprising the biphenyl-containing diarylpyrimido compound of claim 1 or the pharmaceutically-acceptable salt of claim 8 as an active ingredient, and a pharmaceutically-acceptable carrier.

10. A method of treating AIDS in a patient in need thereof, comprising:
   administering a therapeutically effective amount of the pharmaceutical composition of claim 9 to the patient.

* * * * *